United States Patent
McLaughlin

(10) Patent No.: US 7,749,523 B2
(45) Date of Patent: Jul. 6, 2010

(54) EMOLLIENT SKIN CONDITIONING CREAM AND METHOD

(75) Inventor: James Hugh McLaughlin, Brooklyn, CT (US)

(73) Assignee: Crabtree & Evelyn, Ltd., Woodstock, CT (US)

( * ) Notice: Subject to any disclaimer, the term of this patent is extended or adjusted under 35 U.S.C. 154(b) by 0 days.

(21) Appl. No.: 09/964,143

(22) Filed: Sep. 25, 2001

(65) Prior Publication Data

US 2003/0133900 A1 Jul. 17, 2003

(51) Int. Cl.
*A61K 8/02* (2006.01)
*A61K 8/00* (2006.01)

(52) U.S. Cl. .................... 424/401; 510/130
(58) Field of Classification Search ........... 424/401; 510/130
See application file for complete search history.

(56) References Cited

U.S. PATENT DOCUMENTS

| 3,092,111 A | 6/1963 | Saperstein et al. ......... 128/355 |
| 3,645,904 A | 2/1972 | Beach ........................ 252/89 |
| 4,104,403 A | 8/1978 | Barker et al. ............... 424/365 |
| 4,265,899 A | 5/1981 | Lewis et al. ................ 424/270 |
| 4,446,165 A | 5/1984 | Roberts ..................... 426/602 |
| 4,704,224 A * | 11/1987 | Saud .......................... 510/151 |
| 4,822,601 A | 4/1989 | Goode et al. ................ 424/59 |
| 4,992,476 A * | 2/1991 | Geria ......................... 514/782 |
| 5,223,559 A | 6/1993 | Arraudeau et al. ........... 524/47 |
| 5,360,824 A | 11/1994 | Barker ........................ 424/680 |
| 5,510,100 A | 4/1996 | Picard et al. ................ 424/59 |
| 5,593,680 A | 1/1997 | Bara et al. .................. 424/401 |
| 5,679,326 A | 10/1997 | Bara et al. .................. 424/70 |
| 5,711,942 A | 1/1998 | Eicken et al. .............. 424/70.1 |
| 5,720,961 A | 2/1998 | Fowler et al. .............. 424/401 |
| 5,800,608 A | 9/1998 | Bomal et al. ............... 106/492 |
| 5,804,540 A | 9/1998 | Tsaur et al. ................. 510/135 |
| 5,888,951 A * | 3/1999 | Gagnebien et al. .......... 510/130 |
| 5,891,449 A * | 4/1999 | Daniel et al. ............... 424/401 |
| 5,965,500 A * | 10/1999 | Puvvada ..................... 510/130 |
| 6,017,351 A * | 1/2000 | Street ......................... 606/131 |
| 6,033,647 A * | 3/2000 | Touzon et al. ............... 424/45 |
| 6,042,815 A * | 3/2000 | Kellner et al. ............... 424/400 |
| 6,143,308 A | 11/2000 | Vanstraceele et al. ....... 424/401 |
| 6,153,208 A * | 11/2000 | McAtee et al. .............. 424/402 |
| 6,165,510 A | 12/2000 | Baines et al. ............... 424/489 |
| 6,197,281 B1 * | 3/2001 | Stewart et al. ............... 424/59 |
| 6,428,794 B1 | 8/2002 | Klofta et al. ................ 424/401 |

FOREIGN PATENT DOCUMENTS

| BE | 1000757 A6 | 3/1989 |
| DE | 101 33 399 A | 1/2003 |
| EP | 0 295 886 A-2 | 12/1988 |
| GB | 2297975 A | 8/1996 |
| GB | 2317396 A | 3/1998 |
| WO | WO 96 21425 A | 7/1996 |

OTHER PUBLICATIONS

Edward Sagarin, Cosmetics, Science and Technology, copyright 1957, pp. 81-143 and 147-178.

* cited by examiner

*Primary Examiner*—Shengjun Wang
(74) *Attorney, Agent, or Firm*—McDermott Will & Emery LLP

(57) ABSTRACT

A cosmetic exfoliating composition for use in cleansing and conditioning the skin of the hand, face, heels/knees/elbows and/or body of a human being which is stable and which does not leave a greasy or tacky after-feel when said composition is applied to and rinsed from skin with water and the skin is dried.

19 Claims, No Drawings

EMOLLIENT SKIN CONDITIONING CREAM AND METHOD

FIELD OF THE INVENTION

The invention relates to an improvement in topical compositions for conditioning the skin as well as to an improved method for conditioning the skin. The inventive cosmetic compositions are in the form of a substantially stable, extrudable paste or cream suitable for use in the cosmetic and/or dermatological fields for cleansing, softening, smoothing and moisturizing the skin on the hands, face, heels/knees/elbows and/or the body of a human being. More particularly, the inventive compositions also are a suitable base or vehicle for forming a stable suspension of a mildly abrasive, particulate matter to create exfoliating compositions that are effective to cleanse the skin in a non-abrasive manner by removing dirt or foreign matter and dead skin cells in addition to conditioning the skin. Finally, the invention includes a method of conditioning the skin that comprises the step of applying the inventive compositions to either dry skin or previously wetted skin, gently rubbing or massaging the product on the skin, rinsing the product off the skin with tepid water and drying the treated skin.

BACKGROUND OF THE INVENTION

Compositions and techniques for delivering hydrophobic skin benefit agents to the skin are reported in the prior art. The usual skin benefit agents are fatty or oleaginous materials such as emollient oils, e.g., sunflower oil, mineral oil, coconut oil, soybean oil, almond oil, corn oil and oils from nuts or seeds; or oleaginous, emollient organic materials, e.g., fatty acids, fatty acid salts, fatty alcohols and fatty acid esters, e.g., isopropyl myristate. Transfer of the skin benefit agents to the skin is accomplished in the course of using the product. Products generally fall into three classes—leave on products, products that are applied to and removed from the skin and detergent products containing emollient fatty matter emulsified therein dispersed in water used to wash the skin.

Further, it is known to prepare cosmetic or dermatological compositions containing the skin benefit agents in the form of emulsions or creams. The emulsions may be of the oil-in-water type or the water-in-oil type and normally consist of two immiscible phases and a surfactant whose role is to stabilize one phase in the other phase. In cream form, the ultimate product may be in emulsion form or in suspension form wherein a thickener in the form a powder is employed. However, whether in the form of an emulsion, suspension or cream, the ultimate stability at various temperatures in the range of 5° C. to 50° C. may be a problem. Also, in use, the user may experience a more or less an unpleasant greasy effect or tacky effect depending upon the oil or emollient material employed or the emulsifier/thickener material employed or the overall formulation selected. In addition, the emulsifier/thickener whose presence is necessary for stability can prove to be an irritant to the skin. These prior art products are described in chapters 4-6 in "*Cosmetics, Science and Technology*" edited by Edward Sagarin, copyright 1957.

Further, exfoliating compositions also are well known in the art and typically remove dirt, residual make up and dead skin cells by abrasion produced by a wide variety of particulate materials in a variety of states of comminution. Typically, the particulate matter is suspended in the compositions. Again, a vast number of materials of widely varying particle sizes and chemical identities have been used as exfoliating particles. Illustrative of particulate materials that have been used heretofore are the well known mineral-based materials such as aluminum oxide, synthetic alumina, volcanic ash, diatomaceous earth, bentonite, talc, pumice and silica. Other particulate materials that have been employed are powders of organic polymers, namely, polyethylene, polypropylene, polystyrene, organopolysiloxane, nylon, polyvinyl chloride and cellulose as well as co-polymers of acrylonitrile, acrylate, vinylidene chloride and styrene based monomers. Other particulate materials include powders obtained from the apricot, almond, birch, walnut, peach, sunflower and watermelon seeds and powders of inorganic salts such as calcium carbonate, dicalcium phosphate, sodium metaphosphate, zeolite and sodium chloride. As stated above, the foregoing particulate materials have been utilized in a variety of particle sizes, with the small particle sizes being favored because of the emphasis on particles that do not feel gritty. In any event, by integrating the amount of particulate material and the particle size thereof and the fatty vehicle in which the particles are dispersed, a large number of the foregoing particulate materials can be employed in exfoliating compositions that are suitable for use on the skin. Again, the problems encountered with the exfoliating compositions are temperature stability of the product and the effectiveness of the product in use, e.g., deposits a desirable film of fatty matter on the skin while smoothing and softening the skin.

In view of the foregoing discussion, it appears that there still is a need for stable compositions containing emollient material in the form of an extrudable paste or cream that are suitable for cleansing the skin and depositing a film of emollient material on the skin such that the skin has a non-greasy after-feel when the composition is applied to and massaged into the skin, rinsed off the skin with clear, tepid water and the skin is dried. In addition, a need exists for stable, skin exfoliating compositions in the form of a temperature stable, extrudable paste or cream that are suitable for cleansing and conditioning the skin with fatty matter when employed in the method set forth above.

Furthermore, with respect to the skin exfoliating compositions containing particulate matter, it appears that commercial use of water-soluble salts, e.g., sodium chloride, in particulate form in compositions for exfoliating the skin is almost non-existent. For example, the effectiveness of sodium chloride as a skin exfoliant is well known and this material is readily available and economically attractive. Further, from an environmental standpoint sodium chloride is safe and not harmful to the environment. Also, it is water soluble and easily removed from the skin. It seems that the problem associated with the use of sodium chloride in cosmetic compositions for exfoliating the skin is the problem of forming a stable suspension. Where sodium chloride is used as the particulate exfoliating agent, normally it is admixed with the remainder of the exfoliating skin composition just prior to use or the ingredients of the exfoliating composition are applied to skin sequentially without prior mixing. In fact, U.S. Pat. No. 5,360,824 discloses in Example I an exfoliating composition containing sodium chloride that is prepared just prior to use, because that composition separates at 24° C. and at 50° C. within one hour of manufacture.

In conclusion, it appears that a need still exists for a topical skin composition that will cleanse surface grime and oil from the skin and leave a deposit of a thin film of emollient material on the skin which is effective to soften, smooth and moisturize the treated skin without a greasy after-feel when the composition is removed from the skin by rinsing it with tepid water and the skin is dried.

SUMMARY OF THE INVENTION

The present invention relates to a cosmetic composition for use in cleansing and conditioning the skin of the hands, face, heels/knees/elbows and/or the body of a human being that comprises (A) 35%-80% by weight of emollient material; (B) a water soluble surface active agent in a proportion selected from the range of 0.4% to 8.0% by weight, said proportion being effective to deposit a skin softening amount of emollient material on treated skin without a greasy after-feel when the composition is applied to and rinsed from the skin with water and the skin is dried; and (C) a water-insoluble C12-C18 monocarboxylic acid salt, the weight ratio of said emollient material to said carboxylic acid salt being in the range of 7:1 to 1:1 and being adequate to produce a composition in the form of a substantially stable, extrudable paste or cream; said composition being effective to cleanse, soften, moisturize and smooth the skin when the composition is applied to and massaged onto the skin, thereafter rinsed from the skin with tepid water and the skin is dried. Said compositions also function as a base for skin exfoliating compositions containing, in addition, a skin compatible particulate material.

In the preferred cosmetic compositions, the monocarboxylic acid salt is the calcium or magnesium salt of a C14-C18 fatty acid; the emollient material is present in an amount of from 40% to 60% by weight and consists of major proportion of emollient oil and a minor proportion of emollient material selected from the group consisting of C12-C18 fatty acids, C12-C18 fatty alcohols, C12-C18 fatty esters, Shea Butter, lanolin or lanolin derivatives, lecithin and mixtures thereof, the weight ratio of emollient material to monocarboxylic acid salt is in the range of 4:1 to 2.5:1 and adequate to form a composition in the form of an extrudable paste or cream; and the water-soluble surfactant is an anionic surfactant.

More particularly, the invention concerns a cosmetic composition for use in cleansing and conditioning the skin of the hands, face, heels/knees/elbows and/or body of a human being that comprises (A) 35%-80% by weight of emollient material; (B) a water-soluble surface active agent selected from the group consisting of anionic, nonionic, amphoteric, zwitterionic and cationic surfactants in a proportion selected from the range of 0.4% to 8.0% by weight, said proportion being effective to deposit a skin-softening amount of emollient material on the treated skin without a greasy after-feel when said composition is rinsed from the skin with tepid water and the skin is dried; (C) a water-insoluble monocarboxylic acid salt in a weight ratio of emollient material to monocarboxylic acid salt in the range of 7:1 to 1:1 that is adequate to produce a composition in the form of a substantially stable, extrudable paste or cream; and (D) 5% to 50% by weight of a non-irritating, mildly abrasive, skin compatible, particulate material that is effective to cleanse and lubricate the skin without abrading the skin; said composition being effective to cleanse, soften, smooth and moisturize the skin when the composition is applied to and massaged into the skin, thereafter rinsed from the skin with tepid water and the skin is towel dried.

Also within the scope of the invention is a method of cleansing and conditioning the skin of the hands, face, heels/knees/elbows and/or the human body comprising the steps of (1) applying a cosmetic composition onto wet or dry skin of the area of the body to be treated therewith, said composition containing (A) 35%-80% by weight of emollient material, (B) 0.4%-8.0% of a water-soluble surfactant, said proportion being effective to deposit a skin softening amount of emollient material on the treated skin without a greasy after-feel when said composition is applied to and rinsed from the skin with tepid water and the skin is dried, and (C) a water-insoluble C12-C18 monocarboxylic acid salt in a weight ratio of said emollient material to said monocarboxylic acid salt in the range of 7:1 to 1:1 that is adequate to produce a composition in the form of a substantially stable, extrudable paste or cream; (II) massaging said composition into the skin of said area with the hands; (III) rinsing the composition from the treated skin area with tepid water; and (IV) drying the treated skin area, said method being effective to deposit a film of emollient material on the skin thereby cleansing, smoothing, softening and moisturizing said skin without a greasy after-feel. Further, when the cosmetic composition containing the particulate exfoliating material is applied in the foregoing method, the skin is cleansed in addition to being smoothed, softened and moisturized.

In most preferred cosmetic exfoliating compositions, the fatty matter is a mixture of an emollient oil and an emollient material selected from the group consisting C12-C18 fatty acids, C12-C18 fatty alcohols, C12-C18 fatty esters and mixtures thereof that is present in an amount of 40% to 60% by weight; the water soluble surfactant is an anionic detergent; the monocarboxlic acid salt thickener is calcium stearate; and the non-abrasive, skin compatible particulate material is selected from the group consisting of sodium chloride, pumice, a starch material, a vegetable flour and mixtures of the foregoing, with the weight ratio of emollient material to calcium stearate being within the range of about 4:1 to 2.5:1.

The inventive compositions are in a desirable extrudable paste or cream form that exhibits good temperature stability in the temperature range from 4° C. to 50° C. Further, the inventive compositions, with or without suspended particulate matter for exfoliating the skin, are effective to deposit emollient material on skin, thereby rendering the skin smooth, soft and moisturized because of the combination fatty matter thickened with the water-insoluble C12-C18 monocarboxylic acid salt and the presence of a controlled proportion of a water soluble surface active agent. If the proportion of the water soluble surfactant is not controlled within the range of 0.4%-8.0% by weight, after the composition is rinsed from the skin with water and the skin is dried, said skin is either left in a greasy or tacky state with too little surfactant or the skin is substantially devoid of a film of emollient material when too much surfactant is present in the composition. Further, the proportion of the water soluble surfactant also changes with the area of the skin being treated because the affinity of the skin for the emollients varies according the area of the skin to which the composition is applied. For example, the surfactant generally will be from 0.4% to 3.0% by weight in the product for the hands, 4.0% to 8.0% by weight for the body product applied to the torso in the shower. For the face product, the surfactant generally will range from 4.0% to 8.0% by weight and for the heels/knees/elbows product, the surfactant generally will range from 2.0% to 8.0% by weight. Thus, the combination of ingredients is unique and novel and the effectiveness of inventive compositions as skin conditioners is not disclosed in the prior art. Furthermore, the method of conditioning the skin by applying the inventive compositions on the skin followed by massaging the compositions onto the skin before removing the composition with tepid water and drying the treated skin is not expressly set forth in the prior art.

DETAILED DESCRIPTION OF THE INVENTION

The principal ingredient in the inventive cosmetic compositions in the form of an extrudable paste or cream is the emollient material that is skin compatible and non-irritating.

The expression emollient material refers to oleaginous, hydrophobic materials selected from the group consisting of emollient oils; emollient fatty acids, fatty alcohols and fatty acid esters containing a C8-C20 acyl or alkyl group, preferably a C12-C18 acyl or alkyl group; lanolin; cholesterol; hydrophilic lanolin derivatives; phospholipids; and biological extracts. These materials are well known in the art and when deposited upon the skin in a controlled proportion and manner are effective to smooth, soften and moisturize the skin without a greasy after-feel.

Emollient oils include animal oils, vegetable or plant derived oils, hydrocarbon oils and silicone oils. The oils may be low viscosity, e.g., up to 1000 centipoises (cps.) or high viscosity, e.g., 2000 cps to over 10,000 cps. Specific examples of animal and vegetable or plant derived oils include mink oil, turtle oil, coconut oil, jojoba oil, almond oil, peanut oil, wheat germ oil, rice bran oil, corn oil, soybean oil, olive oil, safflower seed oil, sunflower seed oil, cottonseed oil, apricot kernel oil, peach kernel oil, walnut oil, palm kernel oil, poppyseed oil, hazelnut oil, grapeseed oil, canola oil, avocado oil, macadamia seed oil, castor oil and mixtures thereof. Specific examples of hydrocarbon oils are mineral oil, paraffin oils and squalane. Specific examples of silicone oils are polymethylsiloxanes, polymethylphenylsiloxanes, cyclic polysiloxanes, polysiloxanes modified by polyoxyalkylenes or fatty acids or fatty alcohols and mixtures of the foregoing. Where oils contain unsaturated compounds, use of the hydrogenated version of the oil is preferred.

Specific examples of emollient, hydrophobic compounds containing a fatty (C12-C18) acyl or alkyl group include esters such as isopropyl myristate, isopropyl palmitate, sucrose distearate, butyl stearate, hexyl laurate, capric/caprylic triglyceride, 2-ethylhexyl palmitate, diisopropyl adipate, octyl isononanoate, isopropyl isostearate, isocetyl palmitate, distearyl maleate, diglyceryl diisostearate and mixtures thereof. Specific examples of higher C12-C18 fatty alcohols include cetyl alcohol, stearyl alcohol, oleyl alcohol and mixtures of the foregoing. Specific examples of C12-C18 fatty acids include myristic acid, palmitic acid, behenic acid, stearic acid, oleic acid, isostearic and mixtures of the foregoing. Specific examples of hydrophobic, emollient extracts include Shea Butter or *Butyrospermum Parkii* that is a fat derived from karite tree.

Other suitable emollient materials include wax esters, e.g., lanolin; cholesterol and lanolin alcohols; hydrophilic lanolin derivatives, e.g., ethoxylan; and phospholipids, e.g., lecithin and cephalin. Usually any emollient waxes are present only in small amounts.

Generally, the hydrophobic emollient material will comprise an emollient oil. Preferably, the oil will be mixed with one or more of an emollient compound selected from the group consisting fatty acids, fatty alcohols and fatty esters containing a C8-C20 acyl and C8-C20 alkyl fatty group; Shea Butter; lanolin or a lanolin derivative; and lecithin; with the oil being present in major proportion in the mixture. In general, the proportion of the hydrophobic, emollient material in the final cosmetic composition will be 35% to 80%, preferably 40% to 60%, by weight.

The essential water-soluble surface active agent component of the cosmetic composition generally will be selected from the group of water-soluble anionic, nonionic, amphoteric, zwitterionic and cationic surfactants. These water-soluble surfactants are well known in the art and function herein to lower the surface tension of the water when the cosmetic compositions are washed off of the skin with warm water as well as controlling the amount of fatty matter deposited on the various areas of skin treated therewith. Suitable anionic surfactants include the water-soluble salts of a C8-C18 alkyl sulfate, a C8-C18 alkyl polyethenoxy ether sulfate, a C8-C18 alkylbenzene sulfonate, a C10-C20 alkane sulfonate, a C8-C22 alkene sulfonate, a C8-C18 alkyl monoglyceride sulfate, a C8-C18 acyl isethionate, a C8-C18 acyl taurate and a C8-C22 alkyl or dialkyl sulfosuccinate. Other suitable anionic surfactants are the water-soluble salts of C8-C18 monocarboxylic acids. The cation of the water-soluble salts usually will be selected from the group consisting sodium, potassium, ammonium and C2-C3 alkanolammonium. Specific examples of suitable anionic surfactants include sodium lauryl sulfate, sodium C10-C16 alkyl triethenoxy ether sulfate, potassium C10-C20 alkane sulfonate, sodium cocoyl N-methyl taurate, sodium cocoyl isethionate, triethanolammonium C10-C16 alkyl benzene sulfonate and potassium stearate.

The nonionic surfactants that are suitable for use in the inventive compositions include the ethylene oxide condensates or mixed ethylene oxide and propylene oxide condensates with aliphatic alcohols, acids and amides having a C8-C18 alkyl or C8-C18 acyl in the aliphatic group and with C6-C22 alkyl phenols. Other so called nonionic surfactant compounds include the C8-C18 amine oxides. Still other suitable nonionic surfactants are described in U.S. Pat. No. 3,723,325 to Parran and in U.S. Pat. No. 4,565,647 to Llenado, both of which are incorporated by reference herein.

Generally, the suitable amphoteric surfactants that can be used in the cosmetic compositions described herein contain a quaternary nitrogen and include an alkyl or alkenyl group of 7-18 carbon atoms. These amphoteric surfactants are described by the following structural formula:

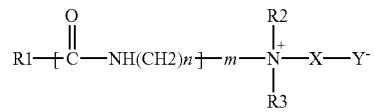

wherein R1 is alkyl or alkenyl of 7-18 carbon atoms, R2 and R3 are each independently alkyl, hydroxyalkyl or carboxyalkyl of 1 to 3 carbon atoms, n is 2 to 4, m is 0 or 1, X is alkylene of 1 to 3 carbon atoms optionally substituted with hydroxyl and Y is —CO2- or —SO3-. Specific examples of suitable surfactants are cocoamidopropyl betaine and cocoamidopropyl hydroxy sultaine (Miranol®CBS).

In general, the suitable zwitterionic surfactants can be broadly described as derivatives of a C8-C18 aliphatic quaternary ammonium, phosphonium and sulfonium compounds containing an anion radical. A general formula for these compounds follows:

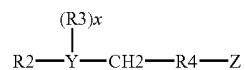

wherein R2 contains an alkyl, alkenyl or hydroxy alkyl radical of from about 8 to 18 carbon atoms and 0-10 ethylene oxide moieties and 0-1 glyceryl moiety; Y is selected from the group consisting of nitrogen, phosphorous and sulfur atoms; R3 is an alkyl or monohydroxy alkyl of about 1 to 3 carbon atoms; X is 1 when Y is a sulfur atom and is 2 when Y is a nitrogen or phosphorous atom; R4 is alkylene or hydroxyalkylene of 1 to 4 carbon atoms; and Z is a radical selected from the group consisting of carboxylate, sulfonate, sulfate, phosphonate and phosphate groups. Examples of zwitterionic surfactants are 3-(N,N-dimethyl-N-hexadecylammonio)propane-1-sulfonate and 5 S-3-hydroxypropyl-S-hexadecylsulfonio-3-hydroxypentane-1-sulfate.

The cationic surfactants that may be employed in the inventive compositions are aliphatic amines including aromatic amines and quaternary ammonium derivatives thereof. Specific examples of cationic surfactants include stearyl dimethylammonium chloride, lauryl dimethylbenzyl ammonium chloride, 2-oleyl imidazoline, lauryl pyridinium bromide, cetyl pyridinium chloride and cetyltrimethyl ammonium chloride.

The non-cationic surfactants are preferred for use in the subject compositions, with the anionic surfactants being most favored. A particularly preferred anionic surfactant is sodium cocoyl N-methyl taurate. Generally, the proportion of surfactant in the final cosmetic composition will be selected from the range of 0.4% to 8.0% by weight, said proportion being effective to deposit a skin softening amount of emollient material on the treated skin after rinsing the treated skin area with warm water and drying same without a greasy after-feel. As stated heretofore, since the skin areas differ in texture, the amounts of surfactant vary with the area of the body being treated as follows: 0.4% to 3.0%, preferably 0.5% to 2.0% and most preferably 0.7% to 1.3%, by weight for the hand buffing composition; 2.0% to 8.0%, preferably 3.0%% to 7.0%, and most preferably 4.0% to 6.0%, by weight for the face and body buffing compositions; and 2.0% to 8.0%, preferably 3.0% to 7.0%, and most preferably 3.5% to 6.0%, by weight for the heels/knees/elbows buffing product. As stated above, the proportion of the surfactant must be controlled so that it is effective to rinse the bulk of the cosmetic composition from the skin after the composition is applied thereto while leaving a deposit of emollient material thereon sufficient to soften, smooth and moisturize the dried skin without an undesirable greasy after-feel. If too little surfactant is present, too much fatty matter remains on the skin in use and the user's skin has a greasy and unacceptable after-feel. On the other hand, if too much surfactant is present, substantially the entire cosmetic composition is removed from the skin when the skin is rinsed with water and dried. Therefore, the proportion of surfactant must be controlled within the specified range because the proportion also varies with the identity of the emollient material present in the inventive composition. For example, more surfactant is required when the viscosity of the fatty matter is high.

The third essential component of the inventive cosmetic compositions is the water-insoluble C12-C18 monocarboxylic acid salt. This ingredient functions to thicken the emollient fatty matter sufficiently to produce the composition in the form of an extrudable paste or cream that is substantially stable at temperatures in the range 4° C.-50° C. The foregoing temperature range embraces the temperatures to which the product is exposed during transportation and storage thereof. Further, it is theorized that the combination of emollient material and monocarboxylic acid salt facilitates the deposit of the emollient material on the user's skin when employed in the method of conditioning set forth herein. Examples of specific thickeners include calcium and magnesium salts of lauric acid, myristic acid, palmitic acid, oleic acid and stearic acid. Preferred salts are the calcium and magnesium salts of the C16-C18 monocarboxylic acids, with the most preferred salt being calcium stearate.

The proportion of the calcium or magnesium C12-C18 monocarboxylic acid salt in the inventive cosmetic compositions is related to the proportion of the emollient material. More particularly, generally the weight ratio of emollient material to the monocarboxylic acid salt will be in the range of about 7:1 to about 1:1, preferably 5:1 to 2:1, and most preferably 4:1 to 2.5:1, by weight and said proportion must be adequate to produce the final composition in the form of a substantially stable, extrudable paste or cream. Thus, the proportion of the water-insoluble monocarboxylic acid salt must be controlled to achieve the desired extrudable paste or cream product.

As stated heretofore, included within the described invention are cosmetic compositions in extrudable paste or cream form that include, in addition, a non-irritating, skin compatible, mildly abrasive, particulate material that is effective as an exfoliating agent to remove dirt and dead skin cells without abrading the skin, said particulate matter being stably suspended in the cosmetic composition. Without the added particulate material, the cleansing action of the cosmetic composition is limited to removal of surface grime and skin oil. Generally, the nature of the particulate material and the particle size will be correlated to impart a mildly abrasive feel to the skin in use so that the user desirably will be aware of and sense the exfoliating particles at work. As stated heretofore, by choosing skin compatible, non-irritating, non-skin abrading particulate material and adjusting the particle size of said material, a wide variety of particulate materials may be employed in the inventive cosmetic exfoliating compositions.

Generally, the particulate material may be either inorganic or organic from a chemical standpoint and may be either water-soluble or water-insoluble. Also, the particles of the particulate material may be lamellar or platelet shaped or of a spherical shape. However, since particles of spherical shape may not impart the desired, mildly abrasive feel to the cosmetic compositions in use, mixtures of materials with spherical and lamellar or platelet shapes desirably will be employed. Suitable inorganic, mineral based particulate materials include silica, pumice, talc, aluminum oxide, volcanic ash, diatomaceous earth, bentonite, synthetic alumina, calcium carbonate, zeolites and mixtures thereof. Other suitable particulate materials are powders obtained from plants and/or plant seeds such as apricot seeds, almond, birch, walnut, peach seeds, sunflower seeds, watermelon seeds, etc. Similar materials are powders of animal origin, e.g., powdered crabshell and powdered eggshell. Suitable organic based particulate materials include powders obtained from polyethylene, nylon, polystyrene, polypropylene, polyvinyl chloride, cellulose, organopolysiloxane elastomers, hollow particles of thermoplastic material, corn starch, potato starch, rice starch, tapioca starch, wheat starch, arrow root starch, acid or enzyme catalyzed hydrolyzed starch derivatives and mixtures of any of the foregoing. The principal water-soluble, inorganic particulate materials include sodium and potassium chlorides, carbonates and phosphates. The particular particulate material employed in the inventive compositions is not critical and can be whatever appeals to the formulator and is consistent with the marketing scheme for the ultimate product. Due to the different shapes of the dispersed particles, e.g., lamellar, platelet and spherical, advantageously mixtures of particulate materials will be employed so as to include spherical particulates in admixture with the lamellar and platelet particulate materials. However, for environmental reasons and skin safety reasons, water-soluble inorganic salts, particularly sodium chloride, are preferred because they are soluble in water and do not pollute the environment after the inventive compositions are rinsed from the skin. Usually, a spherical particulate material such as starch or a hydrolyzed starch will be present in cosmetic compositions containing the water-soluble inorganic salt particles to temper the perception of grittiness felt by ultimate user of the inventive cosmetic compositions.

Generally, the proportion of non-irritating, skin compatible, particulate material in the inventive cosmetic compositions will be from 5% to 50%, preferably 10%-45%, most preferably 15% to 41%, by weight. In mixtures of particulate materials containing a particulate material whose particles are spherical in shape, the proportion of the particulate material with spherical particles will be from 8% or 10% to 20% by weight.

While the preferred, inventive cosmetic compositions are substantially anhydrous because no water is added thereto, the inventive compositions can contain up to about 15% by weight of added water, with the proportion of added water being correlated to the particulate matter being used in the exfoliating compositions. Obviously, the amount of water can be greater when the balance of the inventive composition does not include a water soluble salt. Because the water-soluble salt dissolves in the water, use of high amounts of water in conjunction with water-soluble particulate matter would dilute the effect of that particulate matter. While most preferably the inventive cosmetic compositions will be anhydrous, the inventive skin composition can include up to 15%, preferably 1% to 10%, by weight of water if the formulator so chooses.

In addition to the foregoing described ingredients, the cosmetic compositions can contain any of the usual optional ingredients commonly found skin conditioning products to modify the color, odor or antibacterial properties. For example, perfumes generally will be present in the proportion of about 0.1% to 2% by weight, but the compatibility of the perfume with the balance of the composition must be evaluated. If colored extrudable pastes or creams are desired, dyes or pigments may be present, too, in concentrations from about 0.001% to 0.5% by weight.

Also, preservatives such as parabens, dimethyloldimethylhydantoin, sorbic acid, etc. may be present to eliminate bacterial contamination. One preferred preservative employed in the inventive skin compositions is a mixture of phenoxy ethanol and methyl, ethyl, propyl, butyl and isobutyl parabens. Similarly, where antimicrobial properties are desired, an antimicrobial, e.g., 3,4,5 tribromosalicylanilide, 3,4,4 trichlorocarbanilide, etc., may be included in amounts of 0.2% to 2.0% by weight. Furthermore, antioxidants such as propyl gallate, butylated hydroxyanisole and butylated hydroxytoluene may be employed in amounts of 0.01% to 0.5% by weight to minimize or retard the development of rancidity. Also, humectants such as sorbitol, glycerine and propylene glycol may be employed in amounts of up to 10% by weight. Further optional ingredients are 0.01% to 1.0% of a sequestering agent, e.g., tetrasodium ethylenediamine tetraacetate, and 0.01% to 0.5% by weight of a healing agent, e.g., allantoin or urea.

Due to the fact that the preferred inventive cosmetic compositions are anhydrous, pH is not relevant. However, because the skin pH is in the range of 5 to 6, desirably the pH of inventive compositions containing water will not vary from said range in any significant fashion.

The cosmetic compositions of this invention may be made in any suitable manner by well known techniques used for manufacturing extrudable creams and pastes. Preferably, the emollient oil and any other hydrophobic, emollient materials are added to a jacketed mixing vessel equipped with a homogenizer mixer. The temperature is increased to 70° C. to about 87° C. with agitation. Thereafter, the water soluble surfactant is added with homogenizer agitation followed by the water-insoluble C12-C18 monocarboxylic acid salt while continuing the agitation. Then, the mixture is cooled to about 25° C. to 30° C. while continuing the agitation. Optional ingredients such perfumes and preservatives are added when the temperature reaches 35° C. to 45° C.

If an exfoliating cream is being produced containing particulate matter, the particulate matter is added with homogenizer agitation about 5 to 10 minutes after the monocarboxylic acid salt is added to the fatty matter surfactant mixture. Usually, if more than one particulate material is employed, the particulate materials are added sequentially with continued agitation. As set forth above, homogenizer agitation is continued as the mixture is cooled. The product discharges from the mixer as pumpable cream and is filled into plastic tubular containers for shipment to the ultimate consumers. The inventive compositions extrude from a squeeze tube package as a coherent stream and the cream is retained on the surface of skin after being applied thereto and rubbed thereon. If necessary, the consistency of the cream can be varied by varying the proportions and the identities of the essential ingredients as well as by adding minor proportions of suspending agents or solvents as the case may be.

In use, the product usually is applied to the hands of user and thereafter rubbed into or massaged onto the skin area to which the product is to be applied. Thereafter, the product is rinsed from the area of application with warm or tepid water with or without further massaging and the area patted dry with a towel. The ability of the product to soften and moisturize the skin without a greasy after-feel is assessed by user subjectively based upon the skin feel perceived by the user. As stated heretofore, the skin feel attained by the same product applied to different areas of the skin on the human body is not the same because the skin on hands differs from the skin on the face or the skin on the elbows or the skin on the arms and legs of the torso. To address the differences in the character of the skin on different portions of a human subject, the products differ chiefly in the amount of the surfactant ingredient, with the product for the hands containing less surfactant than the product for the body. Because the products all are being applied to the epidermis—the outer layer of skin—, it is postulated that the differences perceived for the different areas of the skin are due in part to the following: The thickness of the skin varies, e.g., the skin on face is thinner than skin on the hands. Some skin areas are covered with clothing, e.g. the skin on the body. The hair follicles and sebaceous glands vary with the skin area. (The hair follicles and the sebaceous glands control the penetration and absorption of the emollient materials.) Therefore, conceivably it takes a lesser amount of emollient material or fatty matter on the body as compared to the hands to achieve the same level of softness. Furthermore, due to the continuous exposure of the hands and face to atmosphere, those areas of skin continuously are losing fatty matter by evaporation as well as by attrition and, therefore, must have a greater amount deposited to achieve the desired softness which is consistent with a lower level surfactant in the cream used thereon.

As indicated heretofore, the present invention also includes a method for softening and moisturizing the skin and, optionally cleansing the skin if exfoliating particulate matter is included therein, said method comprising the steps of (A) dispensing a skin softening amount of a substantially stable cream containing emollient material thickened with a water-insoluble salt of a monocarboxylic acid and containing 0.4% to 8.0% by weight of a water soluble surfactant into the hands of the user; (B) applying the dispensed composition to the skin to be treated therewith by massaging with the hands and fingers of the user; (C) rinsing said skin composition from the treated skin area with tepid/warm water; and (D) drying the treated skin by patting with a towel. Optionally, the massaging of skin with the hands and fingers of the user is continued during all or part of the rinsing step. The amount of the inventive cream composition employed in the foregoing method varies in direct proportion with the area of the skin being treated. Typically, the amount applied to hands is about two grams to five grams and the time that the product is massaged or rubbed on the skin varies from about fifteen seconds to up to about one minute and preferably from twenty seconds to forty seconds.

The invention is further illustrated by the examples which follow. Unless otherwise stated, the proportions in the examples and elsewhere in the specification are in percent by weight. Furthermore, the examples are illustrative of the invention, but do not limit it.

Example 1

Hand Buffing Cream

A preferred cosmetic hand scrub or buffing composition has the following formula:

| Ingredient | % by weight |
|---|---|
| Macadamia Ternifolia Seed (nut) oil | 35.6 |
| Stearic acid | 0.6 |
| Shea Butter (Butyrospermum Parkii) | 0.7 |
| Caprylic/capric triglyceride | 0.5 |
| Isopropyl myristate | 1.0 |
| Cyclomethicone | 0.4 |
| Cetyl alcohol | 0.2 |
| Polawax (Emulsifying Wax) N.F. | 1.0 |
| Sucrose distearate | 0.2 |
| Behentrimonium methosulfate/cetearyl alcohol (75/25%) | 0.5 |
| Sodium cocoyl N-methyl taurate | 0.7 |
| Potassium stearate | 0.1 |
| Sodium chloride (a) | 25.0 |
| Calcium stearate | 15.0 |
| Maltodextrin starch | 15.0 |
| Avena Sativa (Oat) Kernel Flour | 1.0 |
| Preservative mixture of phenoxy ethanol and methyl, ethyl, propyl, butyl and isobutyl parabens | 1.0 |
| Sea kelp extract in SD 40 alcohol | 0.1 |
| Fragrance | q.s. |
| Total | 100.0 |

(a) Sodium chloride is purchased from U.S. Salt under the trade name Superior TX-10 Salt and the particle size analysis by weight (U.S. Sieve Series) follows: −20 mesh and +30 mesh = 4%; −30 mesh and +40 mesh = 44%; −40 mesh and +60 mesh = 49%; −60 mesh and +100 mesh = 3%.
(b)-Oat flour is purchased from Beacon CMP Corporation under the tradename Tech-O# 11-070 with a particle size of 45 microns.
(c)-Sea kelp extract is purchased from Pure World Botanicals, Inc. under the trade Seaweed Combination Blend MB 1391 and consists of equal proportions of Fucus Vesiculosus (Bladderwrack) Extract, Myerocystis Pyri Ferra (Pacific Sea Kelp) Extract and Algae (Red Algae) Extract in SDA 40A Alcohol.

The foregoing composition is made by mixing the oleaginous phase comprising the macadamia oil, stearic acid, Shea butter, caprylic/capric triglyceride, isopropyl myristate, cyclomethicone, cetyl alcohol, polawax and sucrose distearate together with, behentrimonium methosulfate/cetearyl alcohol and sodium cocoyl N-methyl taurate in a stainless steel mixing vessel while heating to a temperature of 75° C.-82° C., adding calcium stearate, maltodextrin and oat flour while continuing the agitation and thereafter adding the sodium chloride with agitation. The mixture is thereafter cooled to about 24° C.-28° C. with agitation and the sea kelp extract, fragrance and the preservative are added at about 32° C.-40° C. The resultant product is stable after aging at 24° C. as well as at 50° C. and at 4° C. and has a viscosity of 468,000 cps. (Brookfield Viscometer Model LV, helipath stand and spindle T-F at 0.6 rpm.)

When the composition is applied to the hands from a squeeze tube and is rubbed (massaged) into the skin and thereafter is rinsed off with warm water and the hands being towel dried, the hands feel soft, smooth and non-oily. The difference in skin feel is very pronounced if the product is applied to the back of one hand only and that hand is compared with the back of the untreated hand.

To illustrate the skin softening effect of the skin buffing cream composition of Example 1, said composition was presented to panel of twenty women who regularly used skin conditioning products. The women varied in age from 20 to 60 years of age and all of the panelists had used their favorite brand of skin conditioner within the preceding 24 hour period. Before testing the composition of Example 1, the women were asked to massage their hands by gently rubbing each hand over the front and back of the other hand using a hand-washing motion for up to thirty seconds and to then rate the softness of their hands according to following scale:
1—Not soft
2—Somewhat soft
3—Soft
4—Very soft
5—Extremely soft After each panelist had determined their softness rating, each panelist received a squeeze tube containing the Example 1 composition. The test protocol follows: Step 1—Squeeze about three grams of product into one palm; Step 2—Using a handwashing motion gently massage the product into the front and back of your hands for 15 to 30 seconds; Step 3—Rinse the product from the hands with clear, warm water; Step 4—Pat the hands dry with a towel; and Step 5—Wait 15 minutes and gently massage the hands using a handwashing motion for up to 30 seconds and rate the hands for softness according to the foregoing scale. The results of this panel test are reported in Table I below.

TABLE 1

| Panelist | Age Group | Favorite Brand | Rating Brand | Ex. 1 |
|---|---|---|---|---|
| DM | 30-40 | Avon Moisture Therapy ® | 4 | 5 |
| DK | 40-50 | Nivea ® | 3 | 5 |
| TW | 30-40 | Neutrogena ® | 1 | 5 |
| HC | 20-30 | Eucerin ® | 3 | 5 |
| MR | 30-40 | Oil of Olay ® | 2 | 5 |
| BS | 20-30 | Oil of Olay ® | 2 | 5 |
| KB | 20-30 | Jergens ® | 4 | 5 |
| EB | 30-40 | Suave Skin Therapy ® | 4 | 5 |
| AC | 40-50 | Neutrogena ® | 3 | 5 |
| KC | 40-50 | Keri ® | 3 | 5 |
| MN | 30-40 | Lubriderm ® | 3 | 4 |
| CL | 20-30 | Vaseline Intensive Care ® | 3 | 4 |
| JL | 30-40 | St. Ives ® | 3 | 5 |
| BS | 30-40 | Aveno ® | 3 | 5 |
| LR | 40-50 | L'Oreal ® | 1 | 5 |
| JN | 30-40 | Vaseline Intensive Care Advanced ® | 3 | 5 |
| AC | 20-30 | Vaseline Intensive Care ® | 3 | 5 |
| JM | 50-60+ | Neutrogena ® | 2 | 4 |
| JB | 20-30 | Back to Basics ® | 3 | 5 |
| BK | 50-60+ | Vaseline Intensive Care ® | 3 | 5 |

The foregoing results are almost unbelievable because the inventive composition of Example 1 produced softer hands in every instance. These results are truly surprising and document the superior skin conditioning benefits of the inventive compositions.

Example 2

Heels, Knees and Elbows Buffing Cream

When the 25% by weight of sodium chloride in the composition of Example 1 is replaced with 25% by weight of pumice purchased from Hess Pumice Products under the trade name ½ H-Pumice and the proportion sodium cocoyl N-methyl taurate is increased to 3.5% by weight with a decrease in maltodextrin starch to 12.3% by weight, a preferred cosmetic buffing cream particularly suitable for use on the heels, knees and elbows is obtained. Pumice is a highly porous igneous rock that usually contains about 65%-75% SiO2 and 10%-20% AlO2. The particle size of the pumice (U.S. Sieve Series) by weight follows: −40 mesh and +60 mesh=26%; −60 mesh and +100 mesh=70%; through 100 mesh=4%.

Application of the composition of Example 2 to the elbows and knees of a human subject is effective to smooth the skin thereon.

Example 3

Body Buffing Cream

Substitution of 25% by weight of talc for the 25% by weight of sodium chloride with an increase in the proportion of sodium cocoyl N-methy taurate from 0.8% to 7.0% by weight and a corresponding decrease in the amount of maltodextrin starch from 15% to 8.8% by weight in the composition of Example 1 produces another cosmetic cream that is suitable for use as a body buffing composition. The talc is purchased from Suzorite Mineral Products, Inc. under the trade name 3355 Talc USP BC (Suzorite) and has the following particle size distribution (U.S. Sieve Series) by weight: through 325 mesh=97.8%.

The foregoing body buffing cream which is produced according to the process described in Example 1 is substantially stable after aging at 40° C., 24° C. and 4° C. When the resultant composition is applied to the hands, forearms and legs of the user and is followed by rinsing with warm water, the treated skin is characterized by a smooth, non-oily feel.

Examples 4 and 5

Heels, Knees and Elbows Buffing Cream

When 25% by weight of either crushed walnut or apricot seed is substituted for the 25% by weight of sodium chloride in the composition of Example 2, another stable cream suitable for use as a cosmetic buffing cream for the knees and elbows results. The crushed walnut is purchased from Lipo Chemicals, Inc. under the trade name Lipo WSF 35/60 and is characterized by the following particle size analysis (U.S. Sieve Series) by weight: −40 mesh and +60 mesh=90%; −60 mesh and +100 mesh=10%.

The crushed apricot seed is purchased from Lipo Chemical, Inc. under the tradename Lipo APS 40/60 and is characterized by the following particle size analysis (U.S. Sieve Series) by weight: −20 mesh and +30 mesh=2%; −30 mesh and +40 mesh=18%; −40 mesh and +60 mesh=80%.

Example 6

Body Buffing Cream

Substitution of 25% by weight of oat protein purchased from Beacon CMP Corporation under the trade name Tech-O #11-070 for the 25% by weight of talc in the composition of Example 3 results in a body buffing cream that is comparable in use to the composition of Example 3. The oat protein is in particulate form and has a particle size of 45 microns.

The cosmetic cream containing said oat protein is stable at 24° C. and the feel in use is less gritty than the cream containing the sodium chloride. Based upon user comments, both of the creams are safe and effective to soften and moisturize the skin treated therewith in the process of showering.

Example 7

A cost effective cosmetic composition for exfoliating the skin on the heels, knees and elbows has the following composition:

| Ingredient | % by weight |
| --- | --- |
| Safflower oil | 41.0 |
| Calcium stearate | 15.0 |
| Nonionic surfactant (a) | 4.0 |
| Pumice (½ H Pumice) | 40.0 |
| Total | 100.0 |

(a) C11-C15 Alcohol containing 12 moles of ethylene oxide (Tradename Tergitol 15S)

The foregoing composition is prepared by the same process set forth in Example 1. Said composition is temperature stable and extrudes from the tubular package as a homogeneous cream. It softens, smooths and moisturizes the skin when it is applied thereto according the inventive method set forth herein.

Example 8

Substitution of 25.0% by weight of the deformable, hollow particles of the expanded polymers or copolymers disclosed in U.S. Pat. No. 5,679,326, the disclosure of which is incorporated by reference herein, for the 25% by weight of talc in the composition of Example 3 results in a cosmetic cream that is effective for use as a skin exfoliating composition for use on the body to cleanse and soften the skin.

Example 9

Substitution of 25% by weight of the elastomeric organopolysiloxane disclosed in U.S. Pat. No. 6,143,308 which is incorporated herein by reference for the 25% by weight of sodium chloride in the composition of Example 1 with an increase in sodium cocoyl N-methyl taurate from 0.8% to 6.0% by weight and decrease in maltodextrin starch from 15.5% to 10.3% by weight results in a cosmetic buffing cream suitable for use on the face.

Examples 10-12

Examples 10-12 illustrate the inventive cosmetic skin compositions of Example 1 containing minor proportions of water.

| | % by weight | | |
| --- | --- | --- | --- |
| Ingredients (INCI name) | Ex. 10 | Ex. 11 | Ex. 12 |
| Macademia Temifolia Seed (nut) oil | 36.4 | 36.4 | 36.4 |
| Stearic acid | 0.6 | 0.6 | 0.6 |

-continued

| Ingredients (INCI name) | % by weight | | |
|---|---|---|---|
| | Ex. 10 | Ex. 11 | Ex. 12 |
| Shea Butter | 0.7 | 0.7 | 0.7 |
| Caprylic/Capric Triglyceride (Myrifol 318) | 0.5 | 0.5 | 0.5 |
| Isopropyl myristate | 1.0 | 1.0 | 1.0 |
| Cyclomethicone | 0.4 | 0.4 | 0.4 |
| Cetyl alcohol | 0.2 | 0.2 | 0.2 |
| Polawax NF | 1.0 | 1.0 | 1.0 |
| Sucrose distearate | 0.2 | 0.2 | 0.2 |
| Behentrimonium methosulfate/cetearyl alcohol | 0.5 | 0.5 | 0.5 |
| Sodium cocoyl N-methyl taurate | 0.9 | 0.90 | 0.9 |
| Potassium stearate | 0.1 | 0.1 | 0.1 |
| Calcium stearate | 15.0 | 15.0 | 15.0 |
| Maltodextrin starch | 15.0 | 15.0 | 15.0 |
| Sodium chloride | 23.9 | 16.9 | 20.9 |
| Paraben preservative mixture of Example 1 | 1.0 | 1.0 | 1.0 |
| Water | 1.0 | 8.0 | 4.0 |
| Fragrance | q.s. | q.s. | q.s. |
| Total | 100.0 | 100.0 | 100.0 |

The foregoing compositions are made according to the process set forth in Example 1 and the resultant compositions exhibit stability when stored at 40° C., 24° C. and 4° C. These compositions are suitable for use as skin exfoliating compositions when employed in the inventive method set forth herein.

Examples 13-15

The following compositions illustrate stable exfoliating creams that produce good results on the skin treated therewith when used as a body buffing cream (Example 13), a heels, knees and elbows buffing cream (Example 14) and a hand buffing cream (Example 15).

| Ingredient | % by weight | | |
|---|---|---|---|
| | Ex. 13 | Ex. 14 | Ex. 15 |
| Macadamia Temifolia (nut) oil | 37.55 | 36.68 | 36.66 |
| Stearic acid | 0.65 | 0.55 | 0.55 |
| Shea Butter | 0.72 | 0.72 | 0.72 |
| Caprylic/capric triglyceride | 0.46 | 0.46 | 0.46 |
| Isopropyl myristate | 0.96 | 0.96 | 0.96 |
| Cyclomethicone | 0.36 | 0.36 | 0.36 |
| Cetyl alcohol | 0.24 | 0.24 | 0.24 |
| Polawax | 0.96 | 0.96 | 0.96 |
| Sucrose distearate | 0.24 | 0.24 | 0.24 |
| Behentrimonium methosulfate/cetearyl alcohol | 0.48 | 0.48 | 0.48 |
| Sodium cocoyl N-methyl taurate (e) | 7.75 | 5.75 | 0.75 |
| Potassium stearate | 0.13 | 0.13 | 0.13 |
| Calcium stearate | 15.0 | 15.0 | 15.0 |
| Oat flour (a) | 1.0 | 1.0 | 1.0 |
| Maltodextrin starch | 8.0 | 10.0 | 15.0 |
| Pumice (b) | 5.0 | 23.9 | 0 |
| Sodium chloride (c) | 0 | 0 | 24.0 |
| Paraben preservative mixture of Ex. 1 | 1.0 | 1.0 | 1.0 |
| Extract (d) | 0.1 | 0.1 | 0.1 |
| Fragrance (perfume) | q.s. | q.s. | q.s. |
| Total | 100.0 | 100.0 | 100.0 |

(a), (c) and (d) are the same as employed in Example 1 and (b) is the same as employed in Example 2.
(e) Purchased as Tauranol WS H.P. that is 97% surfactant.

Example 16

When the composition of Example I of U.S. Pat. No. 5,360,824 is reproduced containing, by weight, 20% of sodium chloride particles, 40% corn oil and 40% of VASELINE petroleum jelly, the composition separates with the sodium chloride precipitating in less than one hour. This illustrates that stability is a problem in the prior art exfoliating compositions containing sodium chloride as the particulate exfoliating material.

Examples 17-19

The following compositions further illustrate temperature stable, cleansing creams for use as a heels, knees and elbows buffing cream (Example 17), a body buffing cream (Example 18) and a face buffing cream (Example 19).

| Ingredient | % by weight | | |
|---|---|---|---|
| | Ex. 17 | Ex. 18 | Ex. 19 |
| Sweet almond oil | 50.0 | | |
| Soybean oil | | 60.0 | |
| Sesame seed oil | | | 60.0 |
| Sodium cocoyl N-methyl taurate (Tauranol WSP) | 3.5 | 5.0 | 6.0 |
| Calcium stearate | 18.0 | 15.0 | 18.0 |
| Starch | | 17.0(a) | 16.0(b) |
| Pumice (½ H Pumice) | 28.5 | 3.0 | |
| Total | 100.0 | 100.0 | 100.0 |

(a) Maltodextrin starch;
(b) Corn starch

Examples 20-22

Highly preferred cosmetic compositions suitable for use for buffing the body (Example 20), for buffing the heels, knees and elbows (Example 21) and for buffing the face (Example 22) follow:

| Ingredient | % by weight | | |
|---|---|---|---|
| | Ex. 20 | Ex. 21 | Ex. 22 |
| Macadamia Temifolia Seed (nut) oil | 55.2 | 45.0 | 55.2 |
| Stearic acid | 0.6 | 0.6 | 0.6 |
| Shea butter (Butyrospermum Parkii) | 0.7 | 0.7 | 0.7 |
| Caprylic/capric triglyceride | 0.5 | 0.5 | 0.5 |
| Isopropyl myristate | 1.0 | 1.0 | 1.0 |
| Cyclomethicone | 0.4 | 0.4 | 0.4 |
| Cetyl alcohol | 0.2 | 0.2 | 0.2 |
| Polawax (emulsifying wax) N.F. | 1.0 | 1.0 | 1.0 |
| Sucrose distearate | 0.2 | 0.2 | 0.2 |
| Behenetrimonium methosulfate/cetearyl alcohol. | 0.2 | 0.2 | 0.2 |
| Sodium cocoyl N-methyl taurate (Tauranol WSP) | 7.0 | 3.5 | 8.0 |
| Calcium stearate | 15.0 | 18.0 | 18.0 |
| Pumice ½ H | 5.0 | 28.5 | |
| Corn starch (Zea Maya) | 13.0 | | 14.0 |
| Total | 100.0 | 100.0 | 100.0 |

The foregoing compositions are in the form of substantially stable creams that are effective to soften, smooth, moisturize and cleanse the skin when used in the claimed manner.

Examples 23-30

The following compositions exemplify the basic cream formulations without any particulate matter suspended therein. Said compositions are in the form of substantially homogeneous creams that extrude easily from a tubular package and exhibit good temperature stability at temperatures in the range of 5° C. to 50° C. The weight ratio of the emollient oil to the water-insoluble monocarboxylic acid salt, i.e., calcium stearate, thickening agent is set forth and further illustrates the ability of the water-insoluble monocarboxylic acid salt to form a homogeneous cream with the emollient oil and surfactant that is effective to moisturize and soften the skin when used in accordance with the claimed conditioning method.

|  | % by weight | | | | | | | |
|---|---|---|---|---|---|---|---|---|
| Ingredient | Ex. 23 | Ex. 24 | Ex. 25 | Ex. 26 | Ex. 27 | Ex. 28 | Ex. 29 | Ex. 30 |
| Sesame seed oil | 80 | 70 | 60 | 50 | 80 | 70 | 60 | 50 |
| Calcium stearate | 19 | 28 | 36 | 42 | 12 | 26 | 38 | 49 |
| Tauranol WSP (a) | 1 | 2 | 4 | 8 | 8 | 4 | 2 | 1 |
| Total | 100 | 100 | 100 | 100 | 100 | 100 | 100 | 100 |
| Ratio (b) | 4.2:1 | 2.5:1 | 1.7:1 | 1.2:1 | 6.7:1 | 3.3:1 | 1.6:1 | 1.02:1 |
| Viscosity (cps) (c) | 1500 | 30000 | 200000 |  | 500 |  |  | 1500000 |

(a) Sodium cocoyl N-methyl taurate (97% active)
(b) Weight ratio of emollient fatty matter to water-insoluble monocarboxylic acid salt
(c) Brookfield Viscometer Model LV, spindle #2 LVT at 6 rpm (Ex. 23), spindle #3 LVT at 1.5 rpm (Ex. 24), helipath spindle TF at 1.5 rpm (Ex. 25), spindle #2 LVT at 30 rpm (Ex. 27) and helipath spindle TF at 0.3 rpm (Ex. 30)

Examples 31-38

The following examples exemplify the inventive cream compositions containing water-soluble particulate matter suspended therein.

| Ingredient | Ex. 31 | Ex. 32 | Ex. 33 | Ex. 34 | Ex. 35 | Ex. 36 | Ex. 37 | Ex. 38 |
|---|---|---|---|---|---|---|---|---|
| Sweet almond oil | 72 | 63 | 55 | 44 | 71 | 63 | 47 | 44 |
| Calcium stearate | 17 | 25 | 31 | 38 | 11 | 19 | 35 | 45 |
| Tauranol WSP (a) | 1 | 2 | 4 | 8 | 8 | 4 | 2 | 1 |
| Maltodextrin starch | 10 | 10 | 10 | 10 | 10 | 10 | 10 | 10 |
| Total | 100 | 100 | 100 | 100 | 100 | 100 | 100 | 100 |
| Ratio (b) | 4.2:1 | 2.5:1 | 1.8:1 | 1.2:1 | 6.5:1 | 3.3:1 | 1.3:1 | 1.0:1 |

(a) Sodium cocoyl N-methyl taurate (97% active)
(b) Weight ratio of emollient oil to the water-insoluble monocarboxylic acid salt Again, each composition is in the form of a homogeneous cream containing water-soluble starch particles stably suspended therein. As the starch particles are of spherical shape, the resultant compositions are particularly suitable for use of the face in the claimed method.

Examples 39-44

The following examples further exemplify the inventive cream compositions containing sodium chloride, a water-soluble salt, as the suspended particulate matter. Because the suspended sodium chloride particles are more abrasive than the water-soluble starch particles, said compositions are particularly adapted to cleanse the hands.

|  | % by weight | | | | | |
|---|---|---|---|---|---|---|
| Ingredient | Ex. 39 | Ex. 40 | Ex. 41 | Ex. 42 | Ex. 43 | Ex. 44 |
| Soybean oil | 64 | 55 | 46 | 69 | 60 | 44 |
| Calcium stearate | 15 | 23 | 30 | 10 | 18 | 32 |
| Amphoteric surfactant (a) | 1 | 2 | 4 | 1 | 2 | 4 |
| Sodium chloride (b) | 20 | 20 | 20 | 20 | 20 | 20 |
| Total | 100 | 100 | 100 | 100 | 100 | 100 |
| Ratio (c) | 4.3:1 | 2.4:1 | 1.5:1 | 6.9:1 | 3.3:1 | 1.4:1 |

(a) Disodium lauroyl amphodiacetate (tradename is Miranol ® H2M)
(b) Same as in Example 1
(c) Weight ratio of emollient oil to water-insoluble monocarboxylic acid salt

Examples 45-47

The following compositions exemplify inventive compositions containing water-insoluble particulate matter, i.e. pumice (½ H Pumice), stably suspended therein.

|  | % by weight | | |
|---|---|---|---|
| Ingredient | Ex. 45 | Ex. 46 | Ex. 47 |
| Safflower oil | 45 | 38 | 43 |
| Calcium stearate | 14 | 20 | 9 |
| Nonionic surfactant (a) | 1 | 2 | 8 |
| Pumice (½ H Pumice) | 40 | 40 | 40 |

-continued

| | % by weight | | |
|---|---|---|---|
| Ingredient | Ex. 45 | Ex. 46 | Ex. 47 |
| Total | 100 | 100 | 100 |
| Ratio (b) | 3.2:1 | 1.9:1 | 4.8:1 |

(a) C11-C15 alcohol containing 12 moles of ethylene oxide (Tergitol 15S tradename)
(b) Weight ratio of emollient oil to water-insoluble monocarboxylic acid salt.

Each of the foregoing compositions is in the form of an extrudable cream that exhibits stability in the temperature range of 5° C. to 40° C.

When magnesium stearate is substituted for calcium stearate in the compositions of Examples 45-47, similar results are obtained.

The viscosities of the inventive extrudable paste and cream cosmetic compositions vary over a wide range as measured by a Brookfield Viscometer Model LV with and without a helipath stand as the case may be and using various spindles and spindle speeds. Generally, the viscosity of the inventive compositions ranges from 500 cps. to 1,500,000 cps., preferably 50,000 cps. to 1,000,000 cps. and most preferably from 100,000 cps. to 750,000 cps. It is clear from the viscosity data that the inventive cosmetic compositions differ from the prior O/W and W/O emulsion products.

In use, the described topical skin compositions are effective to condition the area of skin of a human being, particularly the hands, face, heels/knees/elbows and the body, to which the composition is applied and leave said skin soft, smooth and moisturized without a greasy after-feel after application in extrudable paste or cream form, massaging, removal with tepid water and drying. Furthermore, addition of non-irritating, mildly abrasive, skin compatible particulate material to the foregoing skin composition produces an exfoliating composition which cleanses the skin in addition. The skin effects produced in use are superior to the prior art compositions because of the use of water-insoluble monocarboxylic acid salt in combination with the emollient fatty matter and the use of said mixture with controlled proportion of surfactant. Further, the method of conditioning the skin also is novel and effective. Thus, the inventive topical skin compositions and the method of using said compositions are new, useful and unobvious from the state of knowledge in the art.

What is claimed is:

1. A cosmetic exfoliating composition which is stable and which does not leave a greasy or tacky after-feel when said composition is applied to and rinsed from skin with water and the skin is dried, said composition comprising:
   (A) an emollient material consisting essentially of:
      (i) 35% to 60% by weight of the composition at least one emollient oil selected from the group consisting of animal oils, vegetable or plant derived oils, hydrocarbon oils, silicone oils and mixtures thereof; and
      (ii) 0% to 5% by weight of the composition of at least one emollient hydrophobic compound selected from the group consisting of C12-C18 fatty acyl or alkyl group esters, C12-C18 fatty acids, C12-C18 fatty alcohols, C12-C18 fatty esters, an emollient extract, and an emollient wax;
   (B) a calcium or magnesium salt of a C14-C18 monocarboxylic acid wherein the weight ratio of emollient material to said monocarboxylic acid salt is in the range of 4:1 to 2:1, said proportion being adequate to produce a composition in the form of a stable, extrudable paste or cream;
   (C) 10% to 45% by weight of a non-irritating, mildly abrasive, skin compatible, particulate material that is effective to cleanse and lubricate the skin without abrading the skin, said particulate material including a mixture of 8% to 20% by weight of a starch material selected from the group consisting of starches and enzyme or acid hydrolyzed starches with another particulate material selected from the group consisting of sodium chloride, pumice, talc and vegetable flour;
   (D) 0.4% to 8.0% by weight of a surface active agent to form a stable composition and to leave a thin film of emollient material on the skin, which is effective to soften, smooth and moisturize the treated skin without a greasy or tacky after-feel when the composition is removed from the skin by rinsing it with water and the skin is dried; and
   (E) 0%-4% by weight of water.

2. The composition according to claim 1, wherein the amount of water in the composition is 0%-1% by weight.

3. The composition according to claim 1 or 2, wherein said C14-C18 monocarboxylic acid salt is calcium stearate.

4. The composition according to claim 1 or 2, wherein the surface active agent is an anionic surfactant.

5. The composition according to claim 4, wherein said anionic surfactant is sodium cocoyl N-methyl taurate.

6. The composition according to claims 1 or 2, wherein the particulate material is sodium chloride and the amount of surface active agent is 0.4%-3.0% by weight for hand buffing with said composition.

7. The composition according to claims 1 or 2, wherein the particulate material is sodium chloride and the amount of surface active agent is 0.4%-2.0% by weight for hand buffing with said composition.

8. The composition according to claims 1 or 2, wherein the particulate material is sodium chloride and the amount of surface active agent is 0.4%-1.3% by weight for hand buffing with said composition.

9. The composition according to claims 1 or 2, wherein the particulate material is pumice and the amount of surface active agent is 2.0%-8.0% by weight for buffing heels, knees and elbows with said composition.

10. The composition according to claims 1 or 2, wherein the particulate material is pumice and the amount of surface active agent is 3.0%-7.0% by weight for buffing heels, knees and elbows with said composition.

11. The composition according to claims 1 or 2, wherein the particulate material is pumice and the amount of surface active agent is 3.0%-6.0% by weight for buffing heels, knees and elbows with said composition.

12. The composition according to claims 1 or 2, wherein the particulate material is pumice and the amount of surface active agent is 2.0%-8.0% by weight for buffing face and body with said composition.

13. The composition according to claims 1 or 2, wherein the particulate material is pumice and the amount of surface active agent is 2.0%-7.0% by weight for buffing face and body with said composition.

14. The composition according to claims 1 or 2, wherein the particulate material is pumice and the amount of surface active agent is 2.0%-6.0% by weight for buffing face and body with said composition.

15. The composition according to claim 1, wherein the emollient oil is a macadamia seed oil and rice bran oil; the fatty acyl or alkyl group esters are isopropyl myristate, sucrose distearate, and caprylic/capric triglyceride; the fatty alcohol is cetyl alcohol; the fatty acid is stearic acid; the emollient extract is Shea butter; the emollient is emulsifying wax; the surface active agent is sodium cocoyl N-methyl taurate; the monocarboxylic acid salt is calcium stearate; the particulate material is pumice; and the composition contains 0%-1% by weight water.

16. The composition according to claim 1, wherein the emollient oil is a macadamia seed oil; the fatty acyl or alkyl group esters are isopropyl myristate, sucrose distearate, and caprylic/capric triglyceride; the fatty alcohol is cetyl alcohol; the fatty acid is stearic acid; the emollient extract is Shea butter; the emollient is emulsifying wax; the surface active agents are sodium cocoyl N-methyl taurate and potassium stearate; the monocarboxylic acid salt is calcium stearate; the particulate material is a mixture of sodium chloride and oat kernel flour; and the composition contains 0%-1% by weight water.

17. A method of cleansing and conditioning the skin of the hands, face, heels/knees/elbows and/or the body of human being that comprises the steps of (I) applying the cosmetic composition of claim 1 to the area of the body to be conditioned; (II) massaging said composition into the skin of said area with the hands; (III) rinsing the composition from the treated skin with clear, tepid water, and (IV) drying said treated area by patting with a towel, said method being effective to deposit a film of emollient material on the skin, thereby cleansing, smoothing, softening and moisturizing said skin.

18. A cosmetic exfoliating composition which is stable and which does not leave a greasy or tacky after-feel when said composition is applied to and rinsed from skin with water and the skin is dried, said composition comprising:
   (A) an emollient material consisting essentially of:
      (i) 35% to 47% by weight of the composition at least one emollient oil selected from the group consisting of animal oils, vegetable or plant derived oils, hydrocarbon oils, silicone oils and mixtures thereof; and
      (ii) 0% to 5% by weight of the composition of at least one emollient hydrophobic compound selected from the group consisting of C12-C18 fatty acyl or alkyl group esters, C12-C18 fatty acids, C12-C18 fatty alcohols, C12-C18 fatty esters, an emollient extract, and an emollient wax;
   (B) a calcium or magnesium salt of a C14-C18 monocarboxylic acid wherein the weight ratio of emollient material to said monocarboxylic acid salt is in the range of 4:1 to 2:1, said proportion being adequate to produce a composition in the form of a stable, extrudable paste or cream;
   (C) 15% to 41% by weight of a non-irritating, mildly abrasive, skin compatible, particulate material that is effective to cleanse and lubricate the skin without abrading the skin, said particulate material including a mixture of 8% to 20% by weight of a starch material selected from the group consisting of starches and enzyme or acid hydrolyzed starches with another particulate material selected from the group consisting of sodium chloride, pumice, talc and vegetable flour;
   (D) 0.4% to 3.0% by weight of a surface active agent to form a stable composition and to leave a thin film of emollient material on the skin, which is effective to soften, smooth and moisturize the treated skin without a greasy or tacky after-feel when the composition is removed from the skin by rinsing it with water and the skin is dried; and
   (E) 0%-1% by weight of water.

19. A cosmetic exfoliating composition which is stable and which does not leave a greasy or tacky after-feel when said composition is applied to and rinsed from skin with water and the skin is dried, said composition comprising:
   (A) an emollient material consisting essentially of:
      (i) 35% to 60% by weight of the composition of macadamia temifolia seed oil; and
      (ii) 0% to 5% by weight of the composition of at least one emollient hydrophobic compound selected from the group consisting of isopropyl myristate, sucrose distearate, caprylic/capric triglyceride, cetyl alcohol, stearic acid, Shea butter, and emulsifying wax;
   (B) a calcium stearate wherein the weight ratio of emollient material to calcium stearate is in the range of 4:1 to 2:1, said proportion being adequate to produce a composition in the form of a stable, extrudable paste or cream;
   (C) 15% to 41% by weight of a non-irritating, mildly abrasive, skin compatible, particulate material that is effective to cleanse and lubricate the skin without abrading the skin, said particulate material is a mixture of sodium chloride and 8% to 20% by weight maltodextrin;
   (D) 0.4% to 3.0% by weight of at least one surface active agent to form a stable composition and to leave a thin film of emollient material on the skin, which is effective to soften, smooth and moisturize the treated skin without a greasy or tacky after-feel when the composition is removed from the skin by rinsing it with water and the skin is dried, selected from sodium cocoyl N-methyl taurate and potassium stearate; and
   (E) 0%-1% by weight of water.

* * * * *